(12) United States Patent
Tauban et al.

(10) Patent No.: US 12,402,798 B2
(45) Date of Patent: Sep. 2, 2025

(54) PRESSURE SENSING LAYER USEFUL IN PRESSURE SENSING DEVICES AND THAT COMPRISES FILM COMPRISING LAYER OF POROUS MATRIX MATERIAL

(71) Applicants: ECOLE SUPERIEURE DE PHYSIQUE ET DE CHIMIE INDUSTRIELLES DE LA VILLE DE PARIS, Paris (FR); CENTRE NATIONAL DE LA RECHERCHE SCIENTIFIQUE, Paris (FR)

(72) Inventors: Mathieu Tauban, Lyons (FR); Mickaël Pruvost, Paris (FR); Annie Colin, Bordeaux (FR); Philippe Poulin, Talence (FR); Lise Trouillet-Fonti, Villette-de-Vienne (FR); Olivier Sanseau, Lyons (FR)

(73) Assignees: L'ÉCOLE SUPÉRIEURE DEPHYSIQUE ET DE CHIMIEINDUSTRIELLES DE LA VILLE DE PARIS, Paris (FR); LE CENTRE NATIONAL DE LARECHERCHE SCIENTIFIQUE, Paris (FR)

( * ) Notice: Subject to any disclaimer, the term of this patent is extended or adjusted under 35 U.S.C. 154(b) by 1153 days.

(21) Appl. No.: 16/958,882

(22) PCT Filed: Apr. 18, 2018

(86) PCT No.: PCT/EP2018/059957
§ 371 (c)(1),
(2) Date: Jun. 29, 2020

(87) PCT Pub. No.: WO2019/129391
PCT Pub. Date: Jul. 4, 2019

(65) Prior Publication Data
US 2020/0337569 A1    Oct. 29, 2020

(30) Foreign Application Priority Data

Jan. 1, 2018 (WO) ............... PCT/EP2018/050002
Jan. 1, 2018 (WO) ............... PCT/EP2018/050003

(51) Int. Cl.
*G01L 1/14* (2006.01)
*A61B 5/00* (2006.01)
(Continued)

(52) U.S. Cl.
CPC ...... *A61B 5/02108* (2013.01); *A61B 5/02028* (2013.01); *A61B 5/02141* (2013.01);
(Continued)

(58) Field of Classification Search
CPC . G01L 1/146; G01L 1/148; G01L 1/14; G01L 1/18; A61B 5/02108;
(Continued)

(56) References Cited

U.S. PATENT DOCUMENTS

| | | | | |
|---|---|---|---|---|
| 8,643,463 B2* | 2/2014 | Samah | ............... | B29D 7/01 338/13 |
| 2015/0320356 A1* | 11/2015 | Toth | ............... | G01L 1/205 600/587 |

FOREIGN PATENT DOCUMENTS

| | | | |
|---|---|---|---|
| CN | 106633891 A | | 5/2017 |
| KR | 2016133094 A | | 11/2016 |

(Continued)

OTHER PUBLICATIONS

Pang, et al., "Highly Skin-Conformal Microhairy Sensor for Pulse Signal Amplification", Advanced Materials, 2015, vol. 27, Issue 4, pp. 634-640.
(Continued)

*Primary Examiner* — Brandi N Hopkins
(74) *Attorney, Agent, or Firm* — Osha Bergman Watanabe & Burton LLP

(57) ABSTRACT

Pressure sensing layers, devices comprising same, pressure sensing monitors and composite materials comprising a) a porous matrix material comprising a siloxane polymer, comprising a closed porosity volume fraction, and, optionally, an open porosity volume fraction, and b) a conductive or semiconductive filler substantially present in the closed porosity volume fraction of the porous matrix material a), and films, coated substrates and multilayer structures comprising the composite material and the use thereof in pressure sensing devices.

25 Claims, 7 Drawing Sheets

(51) Int. Cl.
| | |
|---|---|
| *A61B 5/02* | (2006.01) |
| *A61B 5/021* | (2006.01) |
| *B32B 5/18* | (2006.01) |
| *B32B 27/06* | (2006.01) |
| *B32B 27/36* | (2006.01) |
| *C08J 5/18* | (2006.01) |
| *C08J 9/00* | (2006.01) |
| *C08J 9/28* | (2006.01) |

(52) U.S. Cl.
CPC .............. *A61B 5/6802* (2013.01); *B32B 5/18* (2013.01); *B32B 27/065* (2013.01); *B32B 27/36* (2013.01); *C08J 5/18* (2013.01); *C08J 9/0061* (2013.01); *C08J 9/0066* (2013.01); *C08J 9/009* (2013.01); *C08J 9/283* (2013.01); *G01L 1/146* (2013.01); *G01L 1/148* (2013.01); *A61B 2560/0214* (2013.01); *A61B 2560/0468* (2013.01); *A61B 2562/0247* (2013.01); *A61B 2562/12* (2013.01); *B32B 2266/0214* (2013.01); *B32B 2305/022* (2013.01); *B32B 2307/304* (2013.01); *B32B 2457/00* (2013.01); *C08J 2201/026* (2013.01); *C08J 2201/0504* (2013.01); *C08J 2205/044* (2013.01); *C08J 2205/052* (2013.01); *C08J 2205/06* (2013.01); *C08J 2207/10* (2013.01); *C08J 2383/07* (2013.01); *C08J 2483/05* (2013.01); *C08J 2483/12* (2013.01)

(58) Field of Classification Search
CPC ............ A61B 5/02028; A61B 5/02141; A61B 5/6802; C08J 9/0066; C08J 9/009; C08J 9/40; C08L 1/02; C08K 3/04; C08K 7/24; C08K 3/041; C08K 9/06; G02F 1/0102; G01N 21/554; G01N 27/125; B05D 7/24; C01B 32/194; A61L 27/48; A61L 27/28; F03G 7/00; H01G 11/28

See application file for complete search history.

(56) References Cited

FOREIGN PATENT DOCUMENTS

| | | |
|---|---|---|
| WO | 2017172978 A1 | 10/2017 |
| WO | WO-2021107884 A1 * | 6/2021 |

OTHER PUBLICATIONS

Kwon, et al., "Highly Sensitive, Flexible, and Wearable Pressure Sensor Based on a Giant Piezocapacitive Effect of Three-Dimensional Microporous Elastomeric Dielectric Layer", ACS Applied Materials & Interfaces, 2016, vol. 8, pp. 16922-16931.

Aezinia, PhD thesis, "Design of Interface Circuits for Capacitive Sensing Applications", School of Mechatronic Systems Engineering, Faculty of Applied Sciences, Simon Fraser University, Aug. 8, 2014, pp. 22 to 27.

Cecelja, et al., "Role of Arterial Stiffness in Cardiovascular Disease", Journal of he Royal Society of Medicine Cardiovascular Disease, 2012, 1:11, downloaded from cvd.sagepub.com at SAGE Publications on Jun. 20, 2016, 10 pages.

Donley, et al., "Aerobic exercise training reduces arterial stiffness in metabolic syndrome", Journal of Applied Physiology, vol. 116, No. 11, 2014, pp. 1396-1404.

Baruch, et al., "Validation of the pulse decomposition analysis algorithm using central arterial blood pressure", BioMedical Engineering Online, 2014, 13:96, 19 pages.

Munir, et al., "Peripheral Augmentation Index Defines the Relationship Between Central and Peripheral Pulse Pressure", Hypertension, http://hyper.ahajournals.org, 2008, vol. 51, Issue 1, pp. 112-118.

Lee, B-K, "Computational Fluid Dynamics in Cardiovascular Disease", The Korean Society of Cardiology, 2011, vol. 41, Issue 8, pp. 423-430.

King, et al., "Optical blood pressure estimation with photoplethysmography and FFT-based neural networks", Biomedical Optics Express, 2016, vol. 7. Issue 8, pp. 3007-3020.

Ananth, "Project milestone report for CS229: Blood Pressure detection from PPG signal—Sharath Ananth (SUID: sharath2)", available online at http://cs229.stanford.edu/proj2014/Sharath%20Ananth,Blood%20Pressure%20Detection%20from%20PPG.pdf, 16 pages.

Jin, et al., "Advanced Materials for Health Monitoring with Skin-Based Wearable Devices", Advanced Healthcare Materials, 2017, vol. 6, 20 pages.

King, et al., "Porous PDMS force sensitive resistors", Proceedings of the Eurosensors XXIII conference, Procedia Chemistry, 2009, vol. 1, Issue 1, pp. 568-571.

Dusek, et al., "Carbon Black-PDMS Composite Conformal Pressure Sensor Arrays for Near-Body Flow Detection", EEE, Conference—Oceans—Europe > Oceans 2014—Taipei, Taiwan, Apr. 7-10, 2014, 7 pages.

Lee, B-Y, et al. "Low-cost flexible pressure sensor based on dielectric elastomer film with micro-pores—Sensors and Actuators A: Physical", ScienceDirect, 2016, vol. 240, pp. 103-109.

Majerus, et al., "Flexible, Structured MWCNT/PDMS Sensor for Chronic Vascular Access Monitoring", IEEE 2016 IEEE Sensors Book Series, 2016, Conference 15th IEEE Sensors, Orlando, FL., Oct. 30-Nov. 3, 2016.

Pruvost, SIMM ESPCI Lab, "Formulation of Composites for Vibrational Energy Harvesting", Presentation—European Polymer Congress, Lyon, France, Jul. 2, 2017, 21 pages.

Mickael Pruvost et al.; "Polymeric foams for flexiable and highly sensitive low-pressure;" npj Flexible Electronics; Apr. 4, 2019; (6 pages).

* cited by examiner

PRESSURE SENSING LAYER USEFUL IN PRESSURE SENSING DEVICES AND THAT COMPRISES FILM COMPRISING LAYER OF POROUS MATRIX MATERIAL

This application is a U.S. national stage entry under 35 U.S.C. § 371 of International Application No. PCT/EP2018/059957, filed on Apr. 18, 2018, which claims priority to European Application No. PCT/EP2018/050002, filed on Jan. 1, 2018 and European Application No. PCT/EP2018/050003, filed on Jan. 1, 2018. The entire contents of these applications are explicitly incorporated herein by this reference.

The present invention relates to pressure sensing layers comprising composite materials comprising a porous siloxane polymer matrix with a closed porosity volume fraction and a conductive or semiconductive filler (hereinafter jointly referred to as conductive filler) substantially present in said closed porosity volume fraction of the matrix and to devices comprising said pressure sensing layers.

Pressure sensors have attracted much attention in the recent past due to their potential for a variety of different applications. Especially the demand for pressure sensors with high sensitivity in low pressure regions is very high, which systems are needed i.a. for healthcare and medical diagnosis systems as well as in electronic systems, in particular so called e-skin systems.

Pressure sensing devices are typically categorized into three types, depending on the parameter being used for the sensing. Piezoresistive devices use the change in conductivity upon application of external pressure. Piezoelectric devices use the piezoelectric effect, i.e. the generation of an electric charge in a material upon application of pressure. The sensitivity of a piezoelectric device is limited by the physical properties of the piezoelectric substance at the origin of the effect. Piezocapacitive sensors on the other hand make use of the capacitance change occurring in reaction to the application of pressure and their sensitivity is not theoretically limited. The change of capacitance can be a consequence of the distance of two electrodes of the system forming a capacitor changing in reaction to the application of pressure or due to the modification of the equivalent relative permittivity (dielectric constant) of the dielectric material sandwiched between two electrodes under the application of pressure.

Compared to piezoresistive devices piezocapacitive sensors offer some advantages such as low power consumption and better reproducibility. Compared to piezoelectric devices piezocapacitive sensors are easier to process and easier to shape into different forms. Moreover, they do not require poling or stretching.

The magnitude of the capacitance change is determined by the change in relative permittivity (dielectric constant) and/or in the change in the thickness of a dielectric layer and/or in the change in the surface area of an electrode.

Micro- or nano-structures have been suggested in such devices to improve the sensitivity in particular in the low pressure range. However, this requires usually complex and expensive fabrication processes.

B. Y. Lee et al, Sensors and Actuators A 240 (2016), 103 to 109 describes low-cost pressure sensors based on dielectric elastomer films with micro-pores. Porous films are prepared by using a siloxane elastomer material and water droplets without any additives. Polydimethylsiloxane is used as a base material and water droplets are selected as dispersion substance. A solution of PDMS prepolymers, mixed with a curing agent, and water is stirred in a container. Through the stirring process, micro-droplets of water are uniformly dispersed in the PDMS solution due to the insolubility of water. The solution thus obtained is placed between two glass substrates and thereafter the solution is cured. During curing, the water evaporates and a polymerized porous PDMS film having micro-pores where water was initially present is obtained. This film having a thickness of appr. 100 µm forms the dielectric layer of a capacitive type pressure sensor.

A. J. Gallant, Procedia Chemistry 1 (2009), 568-571 relates to porous PDMS force sensitive resistors. Elastomeric force sensitive resistors are made from a porous matrix of PDMS filled with carbon black. The PDMS matrix has the form of a sponge and is obtained using a sugar scaffold. Sugar cubes are placed in a dish with PDMS precursors and left for one hour to become saturated with the PDMS. The cubes are then cured, excess PDMS is trimmed away and the cubes are put in a beaker with distilled water to dissolve the sugar. The structure thus obtained is the inverse matrix of the sugar cube in which voids are distributed and oriented in a random configuration. To introduce the carbon black particles a suspension of carbon black in water is added dropwise to the water saturated sponge thereby creating a high concentration of carbon within the open porosity volume fraction of the sponge. Once filled, the sponge is left to dry and a thin layer of PDMS is coated thereon and cured to seal the carbon inside the sponge. In the sponge, the pore walls are lined with carbon. Upon application of pressure, the carbon-black lined pore walls come into contact, thereby increasing the number of carbon-carbon connections and the pores become conducting.

S. J. A. Majerus, "Flexible, structured MWCNT/PDMS sensors for chronic vascular access monitoring", IEEE Sensors Book Series: IEEE sensors, published 2016—Conference 15th IEE Sensors conference Orlando, FL Oct. 30-Nov. 3, 2016, relates to piezoresistive flexible pulsation sensors obtained by applying a so called additive manufacturing method for printing PDMS with an internal porous structure. The pores are reported to have average pore sizes of appr. 1 mm. To obtain conductive sensors, multi walled carbon nanotubes are added during the manufacturing process. The resistivity is said to be non-linear and hysteresis was observed. Both are undesired effects.

WO 2017/172978 discloses a wearable apparatus comprising i.a. a transducer circuit having a sensor circuit, the sensor circuit including an electrode and the transducer circuit being configured and arranged to convert changes in capacitance into electric signals, the changes in capacitance being responsive to pressure and/or electric field modulations attributable to hemodynamic or pulse-wave events and an electric signal sensing circuit configured and arranged to sense the hemodynamic or pulse-wave events via the electric signals from the transducer circuit.

Bao et al, Nature Materials 2010, Vol. 9 pp. 859-864 describes highly sensitive flexible pressure sensors with microstructured rubber dielectric layers.

Bao et. Al, Adv. Mater. 2015, 27(4), 634-640 describes microhairy sensors for pulse signal amplification which are however complex and costly in manufacture.

Park et al., ACS Appl. Mater. Interfaces 2016, 8 (26), 16922-31 report a flexible and wearable pressure sensor based on the giant piezocapacitive effect of a three-dimensional (3-D) microporous dielectric elastomer, which is capable of pressure sensing. Due to the presence of micropores within the elastomeric dielectric layer, the piezocapacitive pressure sensor is highly deformable by even very small amounts of pressure, leading to an improved sensitivity.

Figure 1:
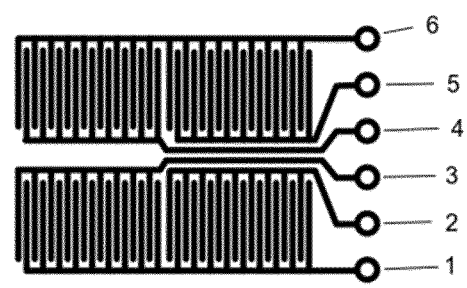
FIG. 1 shows a view of an example for interdigitated electrodes which may be used in the pressure sensing devices in accordance with the present invention.

It was an object of the present invention to provide pressure sensing layers and devices comprising same providing high sensitivity and good reproducibility.

This object is achieved with pressure sensing layers in accordance with claim 1. Preferred embodiments of the invention are set forth in the dependent claims and in the detailed specification hereinafter.

A further object of the present invention are devices comprising the pressure sensing layers in accordance with claim 1.

The pressure which generates a change in capacitance measured by the pressure sensing layers in accordance with the present invention is not particularly limited; it is generally in the range from 10 Pa to 1 MPa. The pressure sensing layer according to the present invention is preferably a low pressure sensing layer. The term "low pressure" as used herein relates to pressures in the range of from 0.01 to 100 kPa, preferably in the range of from 0.05 to 20 kPa, more preferably in the range of from 0.1 to 10 kPa and even more preferably in the range from 0.1 to 1 kPa.

The pressure sensing layer in accordance with the present invention comprises a film comprising
a) a porous matrix material comprising a siloxane polymer, comprising a closed porosity volume fraction, and, optionally, an open porosity volume fraction, and
b) a conductive or semiconductive filler substantially present in said closed porosity volume fraction of said porous matrix material a), and, optionally,
c) one or more additional layers.

Porous materials are usually characterized by their porosity. Porosity or void fraction is a measure of the void (i.e. "empty") spaces in a material, and is the fraction of the volume of voids over the total volume, between 0 and 1, or as a percentage between 0% and 100%.

The apparent porosity or open porosity (oPo) is a fraction of the porosity and is the volume of the open pores, into which a liquid or gas can penetrate, as a percentage of the total volume of the material.

Non-interconnected voids trapped in the solid phase are not part of the open porosity volume fraction; they are part of the closed porosity volume fraction. This fraction also includes any kind of closed pores in the material.

Open porosity and closed porosity sum up to the total porosity of the material.

The porous matrix material in the pressure sensing layer in accordance with the present invention comprises a closed porosity volume fraction, in which a substantial part of the conductive or semiconductive filler is present.

In accordance with a preferred embodiment of the present invention, the closed porosity volume fraction is preferably equal to or greater than the open porosity volume fraction of the material, i.e. the volume of the pores which form the closed porosity volume fraction is preferably at least equal to or greater than the volume of the pores forming the open porosity volume fraction (the ratio of both pore volume fractions thus preferably is at least 1).

In accordance with a particularly preferred embodiment, the ratio of the closed porosity volume to the open porosity volume is in the range of from 1:1 to 100:1, preferably in the range of from 1.5:1 to 50:1 and even more preferably the closed porosity volume comprises 100% of the entire porosity volume, i.e. the product exclusively comprises closed pores.

The open porosity volume fraction of a porous material can be determined by gas displacement pycnometry, a technique known to the skilled person. This technique uses the gas displacement method to measure volume accurately. An inert gas, usually He, is used as the displacement gas. A sample of known weight is sealed in a compartment of the measuring device having a known volume. Then He is allowed to flow into the chamber through an inlet valve until equilibrium is reached, i.e. until the pressure is constant. Then the inlet valve is closed and an outlet valve to a second chamber of precisely known volume is opened. The pressures observed upon filling the sample chamber and then upon discharging the gas into the second empty chamber allow the computation of the sample solid phase volume (which equals the volume of gas displaced by the solid part of the sample plus the volume of the pores not accessible to the gas). Helium gas quickly fills even small pores quickly, only the volume part of the sample which cannot be accessed by the He gas displaces the gas. This part of the sample consists of the solid part of the sample plus the volume represented by the closed porosity volume fraction (as same is defined as being not accessible to the gas).

If the volume displaced by the sample is denoted as $V_s$, the known volume of the sample cell is denoted as $V_c$, the volume of the second compartment into which the gas is displaced is $V_r$, the pressure after filling the sample cell is $P_a$ and the pressure after expansion into the compartment cell is $P_e$, the volume displaced by the sample can be calculated as $$V_s = V_c - V_r(P_e/(P_a - P_e))$$

The displaced or pycnometer volume Vs reflects the volume of the solid part of the porous sample (which is referred to herein as theoretical volume) plus the volume of the closed pores. Theoretical volume can be obtained from the theoretical density of a solid sample without pores, which is usually known for most materials or can be easily determined. Subtracting the theoretical volume from the pycnometer volume yields the volume of the closed pores.

The bulk volume of the porous sample is the geometric volume of the porous sample, which is the sum of theoretical volume plus the volume of the closed pores plus the volume of the open pores. Accordingly, the volume of the open pores can be obtained by subtracting the theoretical volume and the closed pore volume (obtained as explained above) from the bulk (geometrical) volume of the sample.

The closed porosity volume fraction is obtained by dividing the volume of the closed pores by the bulk volume. The open porosity volume fraction can be obtained in an analogous manner. The ratio of both fractions is then obtained by simply dividing the closed pore volume fraction by the open porosity volume fraction.

The total porosity of a porous sample can also be obtained by dividing the bulk density by the theoretical density and subtracting the value from 1.

The foregoing may be explained through the following example: A sample having a theoretical volume of 2 cm$^3$ and a pycnometer volume of 3 cm$^3$ has a closed porosity volume fraction of 1 cm$^3$ (obtained by subtracting the theoretical volume from the pycnometer volume). If the porous sample has a geometric (bulk) volume of 4 cm$^3$, the total porosity, based on the bulk volume, is 2/4 or 0.5. The closed porosity volume fraction, relative to the bulk volume, in this case is 0.25, relative to the total pore volume of the sample, 0.5. This yields a ratio closed porosity volume fraction/open porosity volume fraction of 1.

If, with the same theoretical volume and bulk volume, the pycnometer volume is 3.5 cm$^3$, then the volume of the closed pores is 1.5 cm$^3$ which translates into 37.5%, based on the bulk volume or 75%, based on the total pore volume. In this case the ratio closed porosity volume fraction to open porosity volume fraction is 3:1.

The polymer matrix of the porous material in the pressure sensing layers in accordance with the present invention is a siloxane polymer.

Siloxane polymers or polysiloxanes, also known as silicones, are polymers that include an inert, synthetic compound made up of repeating units of siloxane, frequently combined with carbon or hydrogen or both. They are typically heat-resistant and rubber-like.

A siloxane is a functional group in organosilicon chemistry with the —Si—O—Si-linkage. The word siloxane is derived from the words silicon, oxygen and alkane. Siloxane materials may be composed of several types of so called siloxide groups, depending on the number of Si—O bonds: M-units represented by general structural element $R_3SiO_{0.5}$, D-units by the general structural element $R_2SiO$ and T-units represented by the general structural element $RSiO_{1.5}$.

Siloxane functional groups form the backbone of the silicones.

More precisely polymerized siloxanes or polysiloxanes, silicones consist of an inorganic silicon-oxygen backbone chain ( . . . —Si—O—Si—O—Si—O— . . . ) with organic side groups attached to the silicon atoms. The side groups are preferably selected from alkyl groups or aryl groups or combinations thereof.

In some cases, organic side groups can be used to link two or more of these —Si—O— backbones together. By varying the —Si—O— chain lengths, side groups, and crosslinking, silicones can be synthesized with a wide variety of properties and compositions.

Organic side groups may be alkyl, haloalkyl, aryl, haloaryl, alkoxyl, aralkyl and silacycloalkyl groups as well as more reactive groups such as alkenyl groups such as vinyl, allyl, propenyl, butenyl, pentenyl, hexenyl, heptenyl, octenyl, nonenyl and/or decenyl groups. Polar groups such as acrylate, methacrylate, amino. Imino, hydroxy, epoxy, ester, alkyloxy, isocyanate, phenolic, polyurethane oligomeric, polyamide oligomeric, polyester oligomeric, polyether oligomeric, polyol and carboxypropyl groups may be attached to silicon atoms of the siloxane backbone in any combination.

Siloxanes may be terminated with any useful group such as alkenyl and/or alkyl groups such as methyl, ethyl, isopropyl, n-propyl or vinyl groups or combinations thereof. Other groups that may be used to terminate a siloxane are acrylate, methacrylate, amino. Imino, hydroxy, epoxy, ester, alkyloxy, isocyanate, phenolic, poly polyurethane oligomeric, polyamide oligomeric, polyester oligomeric, polyether oligomeric, polyol and carboxypropyl groups and halo, e.g. fluoro groups.

Polydialkylsiloxanes (where the organic groups are alkyl groups) are a preferred group of siloxane polymers suitable for use in the pressure sensing layers of the present invention.

Polydialkylsiloxane polymers may be represented by the following general formula

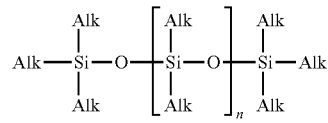

wherein Alk, which may be the same or different at each occurrence, represents a linear, branched or cyclic alkyl group.

Preferred alkyl groups are linear or branched alkyl groups having 1 to 12, preferably 1 to 8 and more preferably 1 to 4 carbon atoms.

The best known example of polydialkylsiloxanes is polydimethylsiloxane (where Alk is a methyl group, hereinafter referred to as PDMS), which is also the most preferred polydialkylsiloxane in accordance with the present invention. The term polydimethylsiloxane or PDMS, when used herein, encompasses derivatives thereof such as hydroxy-, vinyl-allyl- etc. end-capped PDMS.

The porous matrix materials in the pressure sensing layers in accordance with the present invention comprise as component b) a conductive or semiconductive filler substantially present in the closed porosity volume fraction of the microporous polymer matrix a) of the pressure sensing layer in accordance with the present invention.

Substantially present for the purpose of the present invention means that at least 50, preferably at least 60 and even more preferably at least 70% of the conductive filler is present in the closed porosity volume fraction. Up to 99, preferably up to 95 and even more preferably up to 90% of the total content of the conductive filler can present in the closed porosity volume fraction of the composite material a).

The semiconductive or conductive fillers in the pressure sensing layers of the present invention may be selected from any material which has semiconducting or conducting properties.

Thus, a suitable conductive filler may be selected from the list consisting of metal particles like copper, silver, gold, and zinc. Preferably, the conducting metal filler is silver or copper and more preferably is silver.

Conductive polymer particles are essentially composed or even composed of intrinsically conducting polymers (ICPs). They are organic polymers composed of macromolecules having fully conjugated sequences of double bonds along the chains. Such compounds may have metallic conductivity or can be semiconductors. Examples of intrinsically conducting polymers are polyacetylene, polythiophene, polypyrrole, or polyaniline. Among ICPs, polythiophene and polyaniline are preferably used. Poly(3,4-ethylenedioxythiophene) or PEDOT and, in particular PEDOT-PSS, a polymer blend of poly(3,4-ethylenedioxythiophene) and poly(styrene sulfonate) are used more preferably.

Semi-conductive fillers are essentially composed of or composed of a semi-conductive material. The semi-conductive core comprises generally at least 95 wt. % of a semi-conductive material, preferably at least 97 wt. % and more preferably at least 99 wt. %.

Generally, the semi-conductive material is selected from the list consisting of Si, Si—Ge, GaAs, InP, GaN, SiC, ZnS, ZnSe, CdSe, and CdS. Preferably, the semi-conducting material is selected from the list consisting of GaAs, SiC, ZnS and CdS. More preferably, the semi-conducting material is SiC.

Preferably, the semi-conducting filler is selected from the list consisting of GaAs, SiC, ZnS and CdS nanoparticles.

Another group of suitable fillers are metal oxide particles typically containing a metal and an anion of oxygen in the oxidation state of −2, such as ZnO.

In accordance with one embodiment, the conductive or semi-conductive fillers suitable for the invention may have an aspect ratio close to 1. When the aspect ratio is close to 1 the particle tends to be spherical.

In accordance with another embodiment, the conductive or semi-conductive fillers suitable for the invention may have an aspect ratio higher than 1. In this case, the aspect ratio is preferably of at least 5, more preferably of at least 10, even more preferably of at least 15 and the most preferably of at least 20. The particles have usually an aspect ratio of at most 5000, preferably of at most 1000, more preferably of at most 500 and even more preferably of at most 200.

The aspect ratio is the ratio of length to width of a particle (ISO 13794: 1999). An average aspect ratio may be determined by the skilled person by image processing of transmission electron microscopy (TEM) or scanning electron microscopy (SEM) pictures.

In some cases metallic fillers having an aspect ratio higher than one in the form of nanowires have been found advantageous. Particularly preferred nanowires are silver nanowires.

Another group of semiconductive or conductive fillers for use in the pressure sensing layers of the present invention are carbonaceous fillers.

For the purpose of this invention, the term "carbonaceous filler" denotes fillers comprising more than at least 50 wt % of elemental carbon, preferably at last 75 wt % of elemental carbon, more preferably at least 90 wt % of elemental carbon. Especially preferred carbonaceous fillers comprise 99 wt % or more of elemental carbon or consist of elemental carbon.

Preferably the carbonaceous filler is selected from carbon nanotubes, carbon nanohorns, graphite, graphene and carbon black. Particularly preferred for economical reasons is carbon black.

Graphene itself is usually considered as a one-atom thick planar sheet of $sp^2$-bonded carbon atoms that are densely packed in a honeycomb structure. The name graphene is derived from graphite and the suffix -ene. Graphite itself consists of a high number of graphene sheets stacked together.

Graphite, carbon nanotubes, fullerenes and graphene in the sense referred to above share the same basic structural arrangement of their constituent atoms. Each structure begins with six carbon atoms, tightly bound together chemically in the shape of a regular hexagon—an aromatic structure similar to what is generally referred to as benzene.

Carbon nanohorns is the name for horn-shaped aggregates of graphene sheets. Single-walled nanohorns (SWNH) with about 40-50 nm in tubule length and about 2-3 nm in diameter are derived from single walled nanotubes (SWNTs) and ended by a five-pentagon conical cap with a cone opening angle of ~20°. SWNHs may associate with each other to form 'dahlia-like' and 'bud-like' structured aggregates which have an average diameter of about 80-100 nm. The former consists of tubules and graphene sheets protruding from its surface like petals of a dahlia, while the latter is composed of tubules developing inside the particle itself.

Carbon black (CAS 1333-86-4) is a form of paracrystalline carbon that has a high surface-area-to-volume ratio, albeit lower than that of activated carbon.

Chemically, carbon black is a colloidal form of elemental carbon consisting of 95 to 99% carbon. It is usually obtained from the partial combustion or thermal decomposition of hydrocarbons, existing as aggregates of aciniform morphology which are composed of spheroidal primary particles, uniformity of primary particle sizes within a given aggregate and turbostratic layering within the primary particles.

Suitable carbonaceous fillers as described above are available from a variety of sources and suppliers and the skilled person will, based on his professional knowledge and the specific application case, select a suitable material for use in the composite material in accordance with the present invention.

In certain application cases spherical nanoparticulate fillers with an average diameter of 300 nm or less, preferably of 200 nm or less, have been found to provide certain advantages.

The term average particle diameter of a sperical particle when used herein refers to the $D_{50}$ median diameter computed on the basis of the intensity weighed particle size distribution as obtained by the so called Contin data inversion algorithm. Generally said, the $D_{50}$ divides the intensity weighed size distribution into two equal parts, one with sizes smaller than $D_{50}$ and one with sizes larger than $D_{50}$.

In general the average particle diameter as defined above is determined according to the following procedure. First, if needed, the particles are isolated from a medium in which they may be contained (as there are various processes for the manufacture of such particles, the products may be available in different forms, e.g. as neat dry particles or as a suspension in a suitable dispersion medium. The neat particles are then used for the determination of the particle size distribution preferably by the method of dynamic light scattering. In this regard the method as described in ISO Norm Particles size analysis—Dynamic Light Scattering (DLS), ISO 22412:2008(E) is recommended to be followed. This norm provides i.a. for instructions relating to instrument location (section 8.1.), system qualification (section 10), sample requirements (section 8.2.), measurement procedure (section 9 points 1 to 5 and 7) and repeatability (section 11). Measurement temperature is usually at 25° C. and the refractive indices and the viscosity coefficient of the respective dispersion medium used should be known with an accuracy of at least 0.1%. After appropriate temperature equilibration the cell position should be adjusted for optimal scattered light signal according to the system software. Before starting the collection of the time autocorrelation function the time averaged intensity scattered by the sample is recorded 5 times. In order to eliminate possible signals of dust particles moving fortuitously through the measuring volume an intensity threshold of 1.10 times the average of the five measurements of the average scattered intensity may be set. The primary laser source attenuator is normally adjusted by the system software and preferably adjusted in the range of about 10,000 cps. Subsequent measurements of the time autocorrelation functions during which the average intensity threshold set as above is exceeded should be disregarded.

If a treatment is applied to improve e.g. the dispersion of the particles, the measurement of the average diameter of the particles should be carried out after this treatment.

Usually a measurement consists of a suitable number of collections of the autocorrelation function (e.g. a set of 200 collections) of a typical duration of a few seconds each and accepted by the system in accordance with the threshold criterion explained above. Data analysis is then carried out on the whole set of recordings of the time autocorrelation function by use of the Contin algorithm available as a software package, which is normally included in the equipment manufacturer's software package.

The conductive or semiconductive fillers used in the pressure sensing layers accordance with the present invention may deviate from the spherical shape, which is characterized by an aspect ratio of close to 1.

Platy particles are also suitable. Typically, platy particles consist essentially of, or even consist of, particles having the shape of, or resembling to a plate, i.e. the particles are flat or nearly flat and their thickness is small in comparison with the other two dimensions.

Acicular particles are also suitable. Typically, acicular particles consist essentially of, or even consist of, particles having the shape of, or resembling a needle.

Finally, fibrous particles are also well known by the skilled in the art. Typically, fibrous particles consist essentially of, or even consist of, particles having the shape of, or resembling a fibre, i.e. the particles are slender and greatly elongated, and their length is very high in comparison with the other two dimensions. Notably to the purpose of increased reinforcement, the fibrous particles which are advantageously contained in the pressure sensing layer in accordance with the instant invention, have:
- a number average aspect ratio of typically above 5, preferably above 10 and more preferably above 15;
- a number average length of typically at least 50 μm, preferably at least 100 μm and more preferably at least 150 μm; and
- a number average diameter of typically below 25 μm, preferably below 20 μm, and more preferably below 15 μm The average pore diameter, determined using image processing of top view SEM images of the porous matrix materials in the pressure sensing layers in accordance with the present invention, is preferably in the range from 0.1 to 200 μm. preferably in the range from 0.5 to 100 μm and even more preferably in the range of from 1 to 50 μm. In some cases average pore diameters of from 10 to 30 μm have been found beneficial.

SEM is well-suited for quantitative analysis of the pore structure, since it allows a wide range of magnification, a high depth of field, and produces digital data fit for image analysis. SEM combines the best aspects of light microscopy and TEM.

A typical procedure for determining average pore diameter is described in more detail as follows:

A gray scale analysis of the pictures using the software package ImageJ is performed to determine the pore size distribution by thresholding the pictures in order to select the internal area of the pores and then using the Particle Analysis package. This procedure allows the identification of the pore area distribution. Assuming that pores have a spherical shape and are cut through their centers therefore exhibiting their equivalent great circle, the pore size D is extracted as the equivalent diameter from the surface area A, ie D=2 sqrt(A/pi). The average and the standard deviation of pore size are obtained via a statistical analysis accumulating pore size distribution over several pictures (e.g. 10 pictures for a given sample).

In accordance with another preferred embodiment of the present invention, the porous matrix material in the pressure sensing layers of the present invention have a specific electric conductivity, in the absence of external pressure, in the range of from $10^{-5}$ to $10^{-12}$ S/m, preferably in the range of from $10^{-6}$ to $10^{-9}$ S/m.

Electrical conductivity or specific conductance is the reciprocal of electrical resistivity, and measures a material's ability to conduct an electric current.

For piezocapacitive devices, i.e. devices using a change in capacitance upon application of external pressure, it is desirable to obtain a high relative permittivity (dielectric constant) of the material without the material becoming conductive.

It is desirable to obtain a large variation of the relative capacitance change $\Delta C/C_o$ (Co represents the capacitance without application of external pressure whereas $\Delta C$ represents the change in capacitance upon application of a given pressure) under mechanical compression in order to be considered as good piezocapative sensor. Increasing the amount of conductive filler increases the variation of $\Delta C/C_o$.

Relative permittivity is the ratio of the capacitance of a capacitor using that material as a dielectric, compared with a similar capacitor that has vacuum as its dielectric. Relative permittivity is also commonly known as dielectric constant ε. Permittivity is a material property that affects the Coulomb force between two point charges in the material. Relative permittivity is the factor by which the electric field between the charges is decreased relative to vacuum.

Relative permittivity is a dimensionless number that is in general complex-valued; its real and imaginary parts are denoted as $$\varepsilon=\varepsilon'-i\varepsilon''$$

where ε' is the real part of the permittivity and ε" the imaginary part of the permittivity.

The relative permittivity is an essential piece of information when designing capacitors, and in other circumstances where a material might be expected to introduce capacitance into a circuit. If a material with a high relative permittivity is placed in an electric field, the magnitude of that field will be measurably reduced within the volume of the dielectric.

Capacitance is the ability of a body to store an electric charge. The capacitance of a capacitor is a function only of the geometry of the design (e.g. area of the plates and the distance between them) and the permittivity of the dielectric material between the plates of the capacitor.

Capacitance can be calculated if the geometry of the conductors and the dielectric properties of the insulator between the conductors are known. The capacitance C is directly proportional to the relative permittivity and inversely proportional to the distance between the plates of the capacitor.

Upon application of an external pressure, the distance of the pore walls of a pore within the porous matrix material in the pressure sensing layers of the present invention is reduced, thereby increasing the capacitance of the capacitor. This yields the value for $\Delta C$ at a given pressure. The higher the relative permittivity of the material between the plates of the capacitor, the higher $\Delta C$ becomes. Thus, achieving a relative permittivity as high as possible is desired to optimize sensitivity.

The relative permittivity in accordance with the present invention is preferably measured as follows: The sample, preferably in the form of a film, is sandwiched between two metallic disc electrodes and the permittivity is measured in the frequency range from 10 to $10^6$ Hz under an applied voltage of 1 V using an impedance analyzer (BioLogic Impedance analyzer MTZ-35).

The relative permittivity (dielectric constant) of the porous matrix materials in the pressure sensing layers in accordance with the present invention (as well as of the films comprising such porous matrix materials) may span over a wide range without being subject to particular limitations. The higher the permittivity, the higher the sensibility for pressure sensing applications. The upper limit of the permittivity is defined by the composite material comprising the porous matrix material and the filler) becoming conductive i.e. having a conductivity exceeding $10^{-4}$ S/m. Permittivities in the range from 3 to 200, preferably in the range of from 5 to 190 have been achieved.

It is not desirable, however, that the material becomes conductive.

Increasing the amount of conductive filler within the pores increases the relative permittivity but once the percolation point is reached, the material becomes conductive which is undesired. Localizing the conductive filler within the closed porosity volume fraction increases the amount of filler needed to reach the percolation point thereby retaining a low conductivity while significantly increasing relative permittivity, which improves the signal when external pressure is applied and the distance between the pore walls is reduced.

Overall, this leads to a very good sensitivity of the pressure sensing layers comprising the porous matrix material In accordance with a preferred embodiment of the present invention, the amount of filler is in the range of from 0.1 to 15 wt %, preferably in the range of from 0.5 to 12 wt %, based on the entire weight of the porous matrix material and filler.

For an amount of conductive filler close or above the percolation point, an additional layer of a non-conductive material can be coated on top of the pressure sensing layer in order to turn the overall material into a non-conductive final product having low conductivity.

The porous microstructure of the porous matrix materials allows achieving materials with equivalent elastic moduli that cannot be achieved in a homogeneous material. The porous structure allows significant deformations of the dielectric layer in comparison to a non-porous dielectric layer. This increased deformability leads to large changes of the capacitance under compression.

Using an insulating layer of non-conducting material coated on the pressure sensing layer reduces the overall conductivity which allows an increase of the amount of conductive fillers above the percolation threshold within the pores thereby further increasing the relative permittivity.

Suitable non-conductive materials are e.g. polydialkylsiloxanes, in particular polydimethyl siloxane (PDMS) and polyesters, preferably polyethylene terephthalate polymers. Layers of biaxially oriented polyethylene terephthalate films have been found particularly advantageous in certain application cases. Just by way of example for such films, there may be mentioned Mylar®, a product commercially available from DuPont or Hostaphan®, available from Mitsubishi Chemical Corporation.

Another embodiment of the present invention relates to substrates coated with a pressure sensing layer in accordance with the present invention. Details how such substrates can be obtained will be described later in connection with a process in accordance with the present invention to obtain the pressure sensing layers in accordance with the present invention.

Another embodiment of the present invention relates to a pressure sensing device comprising at least one electrode and at least one pressure sensing layer as described above.

Suitable electrodes may be made of an electrically conductive material. Electrodes suitable for the pressure sensing device according to the present invention can be obtained by any method known to the skilled person so that no further details need to be given here.

Suitable electrodes may e.g. comprise materials selected from the group consisting of Au, Ag, Pt, Al, Ni, Pd, Cu, Mo, Ti, Cr, W, Al—Cu alloy, ITO (Indium Tin Oxide), conducting polymers (like PEDOT (poly-3,4-ethylenedioxythiophene), in particular PEDOT-PSS (poly-3,4-ethylenedioxythiophene polystyrene sulfonate) or PANI (polyaniline)) and carbon based materials (like carbon nanotubes, carbon nanohorns, graphite, graphene and carbon black). Preferred electrodes comprise Ag, Au, Pt or PEDOT/PSS and more preferred electrodes comprise Ag or PEDOT/PSS.

The electrodes in the pressure sensing devices in accordance with the present invention usually have an average thickness not exceeding 100 μm, preferably not exceeding 50 μm, more preferably not exceeding 20 μm. The thickness of the electrode layer depends on the electrically conductive material and on the process used for the deposition of the electrically conductive material on the pressure sensing layer. The process used for the deposition can be any of the processes well known to the skilled person.

The electrodes in the pressure sensing devices in accordance with the present invention may either be in close contact with the pressure sensing layer or not.

A spacing layer can be added between at least one electrode and the pressure sensing layer. This allows tuning of the sensitivity. Interfaces between the electrodes and the spacing layer can be adhesive or not and the interfaces between the spacing layer and the pressure sensing layer can be adhesive or not.

According to an embodiment, the pressure sensing layer may be located between a pair of sensing electrodes. Each electrode located on a side of the pressure sensing layer preferably exhibits at least one overlapping portion with at least another electrode located on the other side of the pressure sensing layer.

According to an embodiment, electrodes on at least one side of the pressure sensing layer can be patterned to correspond to an array of conducting pads or more simply may be continuous and unpatterned.

The patterning of an array of conducting pads generates an array of sensors located in the regions of electrode overlap.

Figure 2:
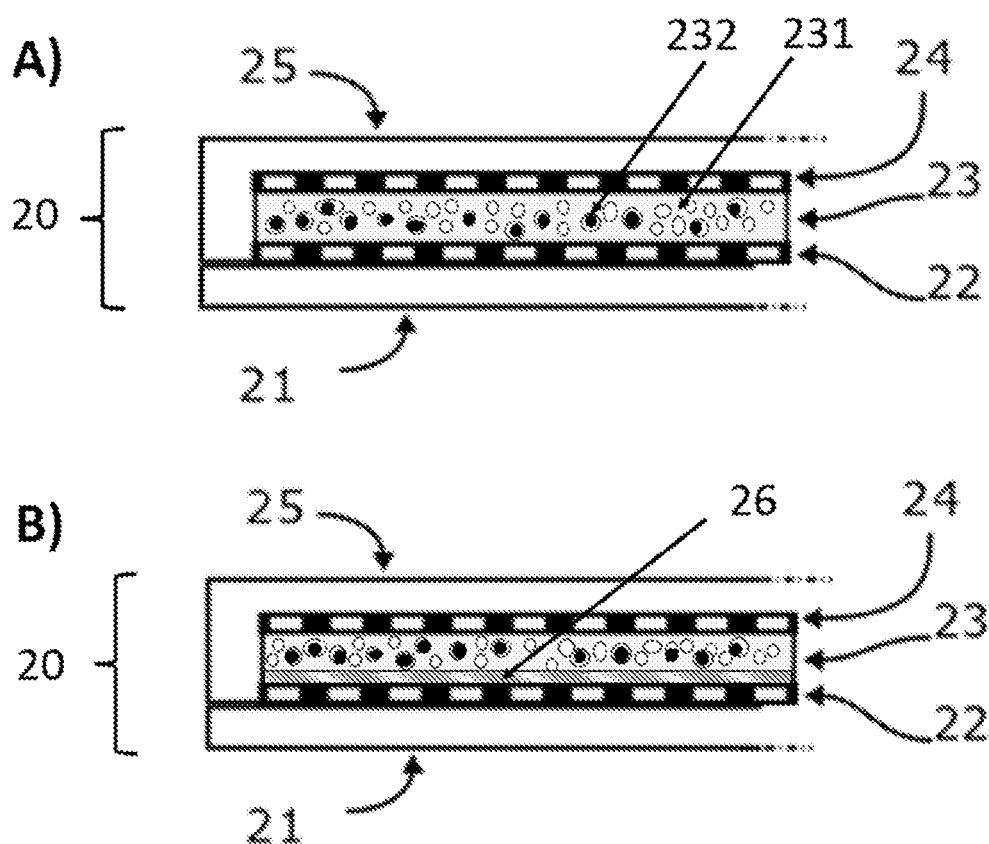
FIG. 2 shows an example of a pressure sensing device in accordance with the present invention with, from top to bottom, showing the following components: encapsulant (25), top electrode (24), pressure sensing layer (23), bottom electrode (22) and protective layer (21).
Figure 3:
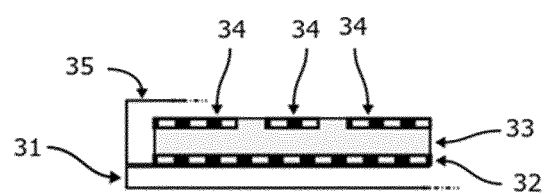
FIG. 3 shows an example of a pressure sensing device in accordance with the present invention with, from top to bottom, showing the following components: encapsulant (35), top electrode (34), pressure sensing layer (33), bottom electrode (32) and protective layer (31), wherein the top electrode (34) is patterned.

FIGS. 2 and 3 show exemplary pressure sensing devices in accordance with the present invention, comprising a protective layer (21, 31), a bottom electrode (22, 32), a pressure sensing layer (23, 33), a top electrode (24, 34) and an encapsulant (25, 35). The dig'ffgerence between the embodiments resides in the fact that in FIG. 3 the top electrode (34) is patterned.

Signals from different sensors of the array can be used in differential mode to eliminate signals that can be common to the sensors of the array such as vibrational noise and temperature changes.

The use of a plurality of electrodes geometrically distributed on the surface of the pressure sensing layer allows to enhance signal detection in case the signal source is localized in a small portion of the pressure sensing layer.

In another embodiment, the pressure sensing layer may be located between an electrode and an array of electrodes.

The change of capacitance due to the pressure signal can be a consequence of the thickness of the pressure sensing layer changing in reaction to the application of the pressure, and/or a consequence of the modification of the equivalent relative permittivity (dielectric constant) of the pressure sensing layer sandwiched between two electrodes under the application of a pressure, which corresponds to the piezocapacitive effect.

In further embodiments, when patterned the sensing electrodes may be located on the same side of the pressure sensing layer and may be preferably interdigitated.

The skilled person, based on his or her professional knowledge, knows suitable techniques to manufacture interdigitated electrodes and, based on the targeted specific application case will select suitable materials and processes so that no further details need to be given here.

In case the electrodes are interdigitated, the signal will come from the deformation of the material located along the electrical field lines, in a region orthogonal to the plane of the electrodes.

FIG. 1 describes an interdigitated sensor array containing four sensor units. The signal can be extracted by measuring the capacitance changes between connector 2 and ground 1 for the first sensor, between connector 3 and ground 1 for the second sensor, connector 4 and ground 6 for the third sensor and connector 5 and ground 6 for the fourth sensor.

In an embodiment where the pressure sensing device comprises only one electrode, the pressure sensing layer is located between the electrode and the origin of the pressure signal.

As for the embodiment with more than one electrode described above, the electrode can be either in close contact with the pressure sensing layer or not and a spacing layer can be added between the electrode and the pressure sensing layer. This allows tuning of the sensitivity. Interfaces between the electrode and the spacing layer can be adhesive or not and the interfaces between the spacing layer and the pressure sensing layer can be adhesive or not.

If only one electrode is present, the electrode has to be "sufficiently close" to the origin of the pressure signal for electrically sensing the pressure via capacitance changes carried out by the electrode.

The pressure sensing layer may be used in combination with the electrode in order to allow a better signal extraction.

More specifically, the pressure sensing layer modulates mechanically the sensitivity of the electrode, modulates signal to noise ratio, and, or reduces signal intensity, depending on its thickness and composition by coupling mechanically the electrode with the origin of the pressure signal, or the pressure sensing layer modulates electrically the sensitivity of the electrode, modulates signal to noise ratio and or reduces signal intensity, depending on its thickness and composition by changing the fringing field distribution between the electrode and the origin of the pressure signal, or the pressure sensing layer can isolate mechanically and electrically the electrode from the origin of the pressure signal, enhancing the robustness of the signal extraction by the electrode, or the pressure sensing layer can be used to adapt the stiffness and or comfortability and or conformability of an apparatus by changing its thickness and or composition, especially in the case of a wearable apparatus.

The porous matrix material in the pressure sensing layer exhibits a high relative permittivity that can be tuned by changing slightly the composition while having a electrical conductivity. Moreover, its equivalent elastic modulus can also be easily tuned by changing slightly the composition.

The tunable relative permittivity can be used to optimize and modulate the fringing field distribution between the electrode and the origin of the pressure signal. The very low and tunable elastic modulus can be used to accommodate with the surface at the origin of the pressure signal.

The electrode located on one side of the pressure sensing layer can be patterned to correspond to an array of conducting pads or more simply can be continuous and unpatterned.

The patterning of an array of conducting pads generates an array of sensors. In this case, the pressure sensing layer can be used as a electromagnetic shield to isolate the electrode.

Signals from different sensors of the array can be used in differential mode to eliminate signals that can be common to the sensors of the array such as vibrational noise and temperature changes. When using multiple thicknesses of the active sensing layer or multiple compositions of the active sensing layer, the sensor circuit with less sensitivity may be used to remove the baseline shifts due to changes in environmental conditions.

The use of a plurality of sensors geometrically distributed on the surface of the pressure sensing layer allows to enhance signal detection in case the signal source is localized in a small portion of the pressure sensing layer.

The use of a plurality of sensors geometrically distributed on the surface of the pressure sensing layer allows to spatially localize the origin of the signal source and to discriminate between signal sources when multiple signal sources are considered.

The pressure sensing layer and the pressure sensing devices described above may comprise an additional layer which usually serves the purpose of a protective layer.

Such protective layer can be used to provide environmental stability and resistance to moisture. In case of a wearable device, it is preferably a skin compatible polymer layer. It may e.g. comprise materials selected from the list consisting of polyolefins like PE or PP, polyesters like PET, siloxane polymers, like PDMS, polyimides, fluorinated polymers, like VDF based polymers or PTFE or polyamides. In a particular embodiment, the protective layer may be the pressure sensing layer. In another particular embodiment, the protective layer may act as the bottom electrode layer Such protective layer has usually an average thickness not exceeding 100 µm, preferably not exceeding 50 µm, more preferably not exceeding 20 µm. The protective layer can be very thin as long as it keeps its functional properties.

The pressure sensing layer or the pressure sensing device may be encapsulated in an encapsulant material. FIGS. 2 and 3 show exemplary embodiments. The encapsulant material can be the same or different than the material of the protective layer.

In a preferred embodiment, the encapsulant layer and protective layer are made of the same material.

In a preferred embodiment, the array of electrodes is located on the top of the system and the bottom electrode is continuous.

When the capacitance change is small due to the pressure signal, it can be advantageous to amplify and or filter the signal. For example, the capacitance change signal can be amplified by mounting the active sensing layer on the gate of a field effect transistor (FET).

Another embodiment of the present invention relates to a pressure sensing monitor comprising
  a) at least one pressure sensing layer or a pressure sensing device in accordance with the present invention providing a capacitance change signal in response to a pressure variation,
  b) a power supply,
  c) at least one signal converting unit capable of converting the capacitance change signal provided by the pressure sensing layer into an analog or digital electric signal, optionally with filters and amplifiers for the signal,
  d) at least one microcontroller unit capable of digitalizing an analog signal provided by signal converting unit c) and/or communicating digitally with the at least one signal converting unit c) and capable to convert the signal obtained from the at least one signal converting unit c) into other formats using suitable algorithms stored in the at least one controlling unit as readable code,
  and, optionally,
  e) at least one data transmission means for transmitting data provided by the microcontroller unit to a data receiving device, and/or
  f) means for communicating data provided by microcontroller unit d) or at least one data transmission means e) to a user.

FIGS. 4 to 7 show exemplary embodiments of the pressure sensing monitors in accordance with the present invention in the form of wearable devices.

The pressure sensing device (401, 501, 601 and 701) comprises one or more electrodes (402, 502, 602, 702), a pressure sensing layer in accordance with the present invention (403, 503, 603, 703) and a protective layer (404, 504, 604 and 704). Changes in capacitance (405, 505, 605 and 705) due to pressure changes are sensed and forwarded to an electronic device (410, 510, 610 and 710) comprising a signal converting unit (406, 506, 606 and 706) which comprises a data transmission unit (407, 507, 607 and 707), a microcontroller unit (408, 508, 608 and 708) and a power supply (409, 509, 609 and 709).

Figure 4:
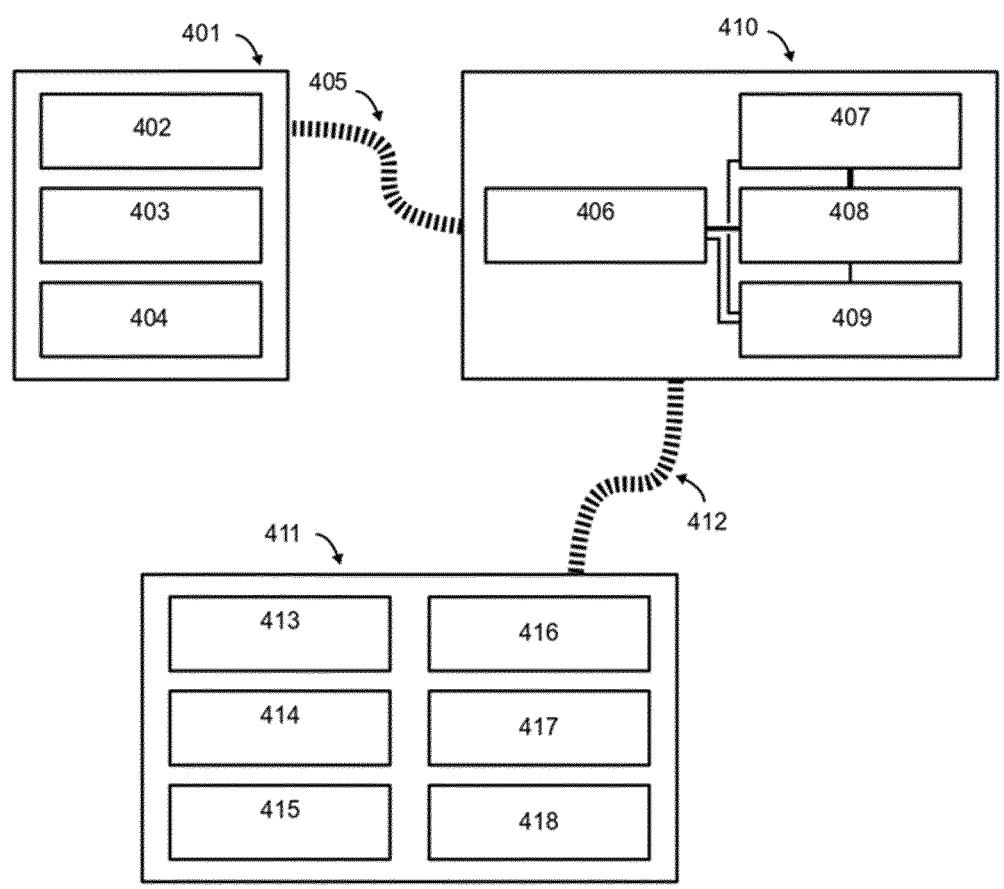
FIGS. 4 to 7 show a block diagram view of embodiments of the pressure sensing monitor in accordance with the present invention in the form of wearable devices, showing the components of the respective monitors.

According to the embodiment of FIG. 4 communication signals (412) are forwarded to a smartphone (411) which represents a means for communicating data. The smartphone comprises a data transmission unit (413) means for patient authentification (414), patient notification (415), data analysis (416), result analysis (417) and data storage (418).

Figure 5:
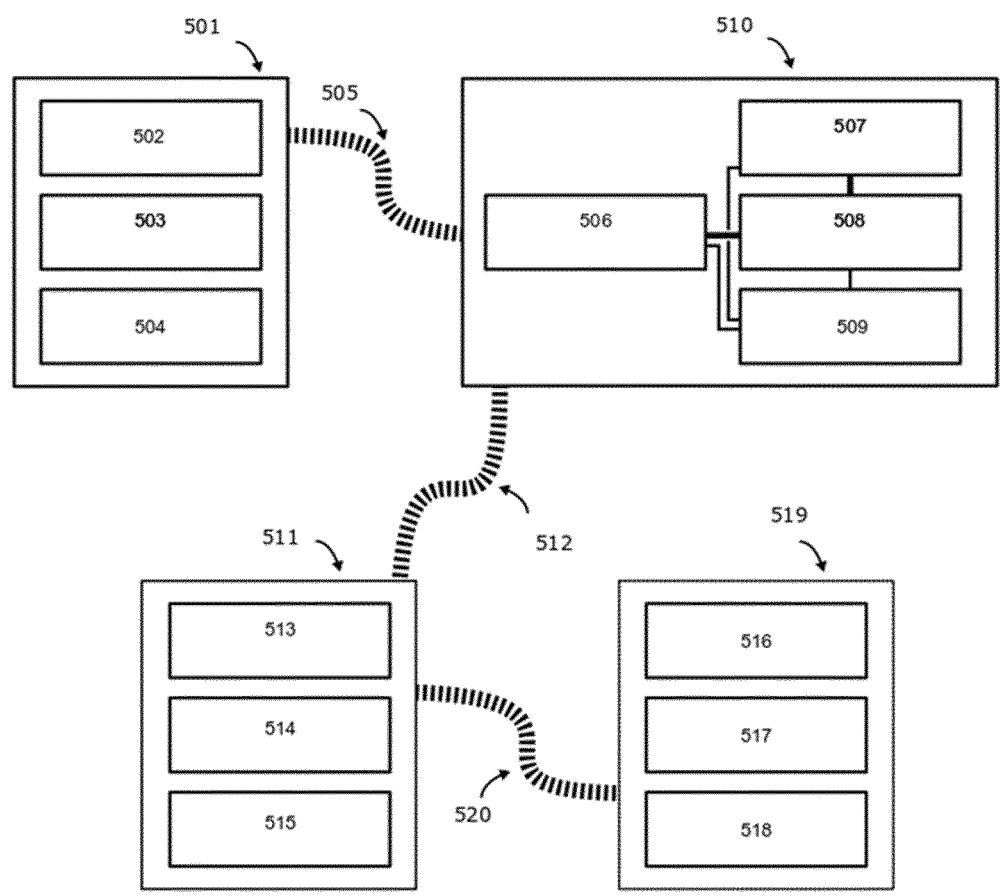

In the embodiment of FIG. 5, communication signals (512) are forwarded to a smartphone (511) which represents a means for communicating data. The smartphone comprises a data transmission unit (513) means for patient authentification (514) and patient notification (515) and has an internet connection (520) to means for data analysis (516), result analysis (517) and data storage (518) as elements of a cloud (519).

Figure 6:
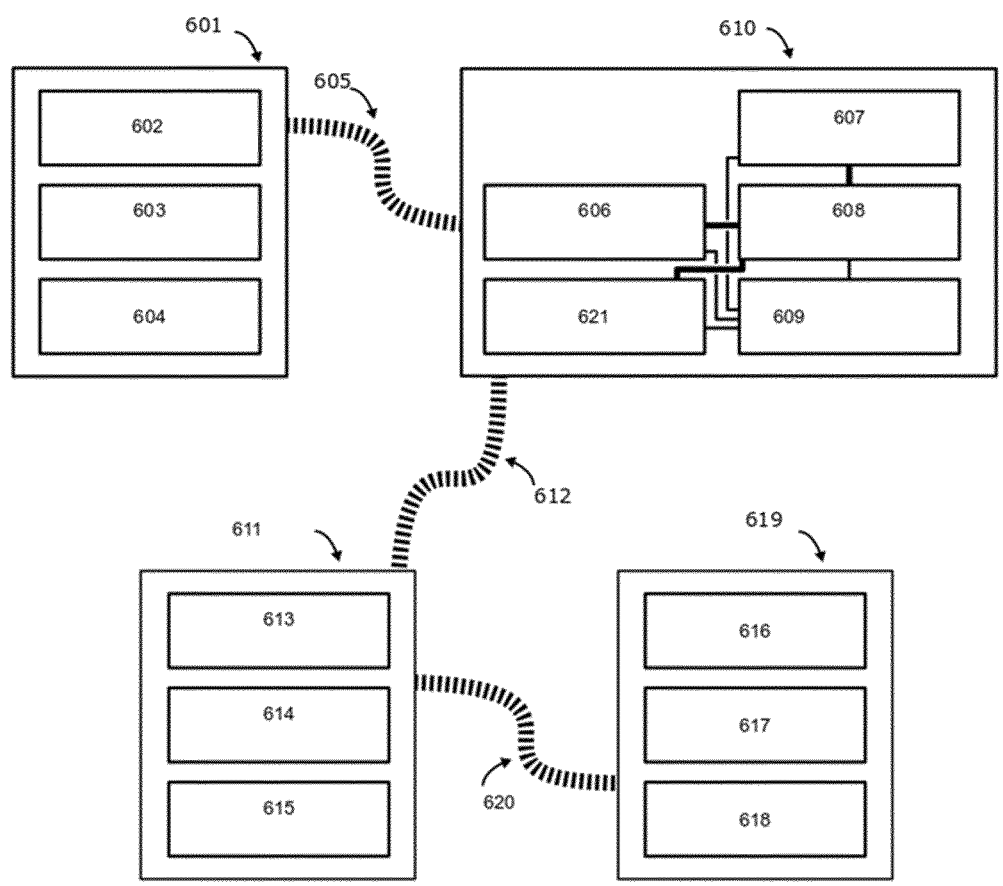

According to the embodiment of FIG. 6, the electronic device additionally comprises a memory unit (621). communication signals (612) are forwarded to a smartphone (611) which represents a means for communicating data. The smartphone comprises a data transmission unit (613) means for patient authentification (614) and patient notification (615) and has an internet connection (620) to means for data analysis (616), result analysis (617) and data storage (618) as elements of a cloud (619).

Figure 7:
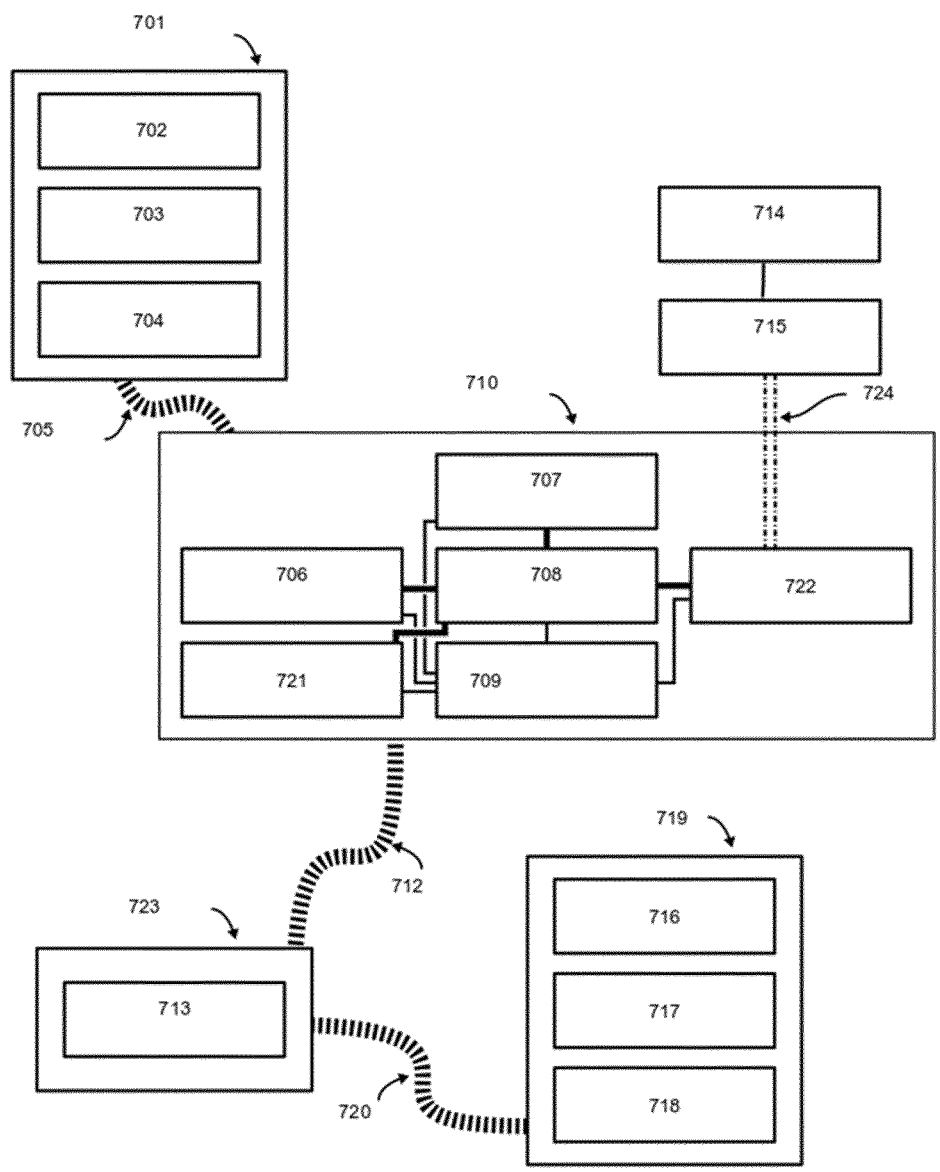

In the embodiment of FIG. 7, the electronic device 710 comprises additionally a display device (722) which, through a user interface (724), is connected to means for patient authentification (714) and patent notification (715). Communication signals (712) are forwarded to a gateway (723) comprising a data transmission unit (713) which trough an internet connev'ction is connected to a cloud (719) comprising means for data analysis (716), result analysis (717) and data storage (718).

In the block diagrams of FIGS. 4 to 7 the pressure sensing device is referred to as sensor, the power supply is referred to as battery, the signal converting unit is denoted as signal conditioning, the microcontroller unit is referred to as MCU and the data transmission means is referred to as communication. The smartphone represents the means for communicating data.

The power supply of the pressure sensing monitor of the present invention provides power to the elements of the monitor. It is preferably made of a rechargeable battery unit or a primary battery unit and may contain a power management unit. Preferably the power management unit is able of modifying the received electrical energy from an external power supply to values acceptable to the rechargeable battery unit. The rechargeable battery unit and or the primary battery unit can be flexible. The primary battery unit may be any primary electrical energy storage cell. The rechargeable battery unit may be any rechargeable electrical energy storage cell. Any power management unit known and described in the literature can be used.

The signal converting unit converts a change in capacitance to an analog or digital signal. It can be selected e.g. from the group consisting of alternating currents bridge sensing circuit, a capacitance to voltage converter, a capacitance to frequency converter, a capacitance to current converter, a capacitance to pulse width converter, a capacitive to digital converter, a differential capacitive sensing converter, a low power differential capacitance sensing low noise or a low power differential capacitance sensing circuit. Respective units are known to the skilled person and have been described in the literature and are commercially available from various sources so that no further details need to be given here.

The PhD thesis of F. Aezinia (Design of Interface circuits for capacitive sensing applications, pages 22 to 27 describes some exemplary suitable signal converting units.

The microcontroller unit d) may be used to digitize the signal. It may perform mathematical computation on the digital data such as an integration of the sensor data, or signal transformation such as a Fourier Transform. This is usually achieved using suitable algorithms stored in the microcontroller unit as readable code.

Optionally data transmission means e) may be present to transmit the processed data of the microcontroller unit d) to a data receiving device such as e.g. a host computing device, e.g. the processed data may be formatted for Bluetooth® radio communication.

The data transmission means may be used to connect to other devices e.g. to a service provider to provide various services related to the pressure signal sensed by the pressure sensing monitor. The service provider may be e.g. a clinic to allow the clinic to provide various services related to the health monitoring of a user of the pressure sensing monitor. The data transmission means may also transmit the information about the acquired signal and calculated data from the sensed pressure signal to an external device such as a smartphone or a computer by formatting the data for Bluetooth® radio communication. Suitable transmission means are known to the skilled person and commercially available from a variety of sources so that no further details need to be given here. The skilled person will select the data transmission means based on his or her professional experience and on the specific application case for which the device is intended.

Optionally means f) for communicating data provided by the microcontroller unit d) or the at least one data transmission means e) to a user may be present. Such means may e.g. be a display showing information about the acquired signal and e.g. of data calculated therefrom reflecting the sensed pressure signal (which sensed pressure signal may e.g. be derived from a hemodynamic activity as described hereinafter). Again, respective means respectively devices for displaying data in a suitable manner are known and have been described in the prior art so that no further details need to be given here. The skilled person will select the suitable display device, if present, based on his professional knowledge and the specific application case.

In accordance with a preferred embodiment, the pressure variation is a pulse wave event and thus the pressure sensing device or the pressure sensing monitor yields a pulse waveform signal created by small pressure variations. This signal can then be used to calculate e.g. various hemodynamic parameters from hemodynamic activity such as heart rate, heart rate variability and blood pressure.

The term "pulse wave event", when used herein, refers to or includes preferably hemodynamic responses and/or attributes caused by or indicative of heart beats (e.g. contraction of heart muscles, heart beats or sounds, changes in blood pressure or blood flow velocity, etc.).

The term "pulse waveform" refers to or includes a signal or wave shape generated by the pulse wave events, such as e.g. an arterial pulse waveform generated by the heart when the heart contracts and the wave travels along the arterial walls of the arterial tree.

The terms "hemodynamic or hemodynamic parameters" refers to or includes parameters relating to the flow of blood within the organs, blood vessels and tissues of the body. Exemplary hemodynamic parameters include but are not limited to diastolic blood pressure, systolic blood pressure, arterial stiffness and blood volume.

In accordance with another preferred embodiment the at least one microcontroller unit c) converts the signal obtained from the at least one signal converting unit b) into hemodynamic parameters.

The microcontroller unit c) may comprise a microcomputer or other CPU including memory circuitry to store program code (a program to be executed as a set or sets of instructions) for performing an algorithm (e.g. monitoring pressure differentials and or capacity changes attributable to pulse-wave events) and/or involving hemodynamic parameters and/or more complex algorithms as have been described in the literature relating to such specific parameter sensing. Such processes/algorithms would be specifically implemented to perform the related steps, functions, operations, activities as appropriate for the specific application.

Heart rate can be calculated from the Fourier transform of the pulse-waveform. The heart rate corresponds to the inverse frequency at which the Fourier transform of the pulse waveform exhibits a peak. This calculation step can be advantageously used to proceed to a filter of the signal, using for instance a low pass filter on the fourier transform of the pulse waveform, using a cutoff frequency of, for instance, 10 Hz. The heart-rate value can be averaged over a period of time (e.g., 15 seconds).

The heart rate variability can be determined from the distribution of individual heart rate values.

The blood pressure can be calculated from pulse waveform in various ways.

The shape and other features of the pulse-waveform can be correlated to blood pressure.

Variations of blood pressure can be monitored by first calibrating the data such as with arterial lines that are calibrated against inflatable cuff data.

Various different techniques can be used to analyze the pulse-waveform and/or to determine various hemodynamic parameters including feature analysis and computation fluid dynamics techniques. For example, features attributed to hemodynamic phenomena can be correlated to blood pressure, arterial stiffness, and other hemodynamic parameters. For more general and specific information on features attributed to hemodynamic phenomena, reference is made to Cecelia, Marina, and Phil Chowienczyk. "Role of Arterial Stiffness in Cardiovascular Disease." JRSM Cardiovascular Disease 1.4 (2012): cvd.2012.012016, PMC, Web. 31 Jan. 2017; David A. Donley et al, "Aerobic exercise training reduces arterial stiffness in metabolic syndrome" Journal of Applied Physiology published 1 Jun. 2014, Voll 16, no. 11, 1396-1404; Baruch, Martin C, et al "Validation of the pulse decomposition analysis algorithm using central arterial blood pressure." Biomedical engineering oriHne 13.1 (2014): 96., and Munir, Sbahzad, et al. "Peripheral augmentation index defines the relationship between central and peripheral pulse pressure." Hypertension 51.1 (2008): 112-118, each of which are fully incorporated herein. As another example, the augmentation index (AI), (peripheral second systolic blood pressure (pSBP2)–diastolic blood pressure (DBP))/(peripheral systolic blood pressure (pSBP)–DBP) can be used as a marker for arterial stiffness and may be correlated to both peripheral and central peak blood pressure (pPP & cPP). Al is a normalized parameter and can be analyzed without absolute calibration. Computation fluid dynamic techniques can include modeling vasculature as an inductor capacitor resistor (LCR) circuit and/or as a network of elastic pipes to calculated parameters such as pulse-wave velocity and/or waveform shape. For more general and specific information related to computation fluid dynamics used to determine hemodynamic parameters, reference is made to Lee, Byoung-Kwon, "Computational fluid dynamics in cardiovascular disease", Korean circulation journal 41.8 (2011): 423-430, and Xiaoman Xing and Mingshan Sun, "Optical blood pressure estimation with photoplethysmography and FFT-based neural networks," Biomed. Opt. Express 7, 3007-3020 (2016), each of which are fully incorporated herein for further information.

One model that can be used to derive a relationship between the pulse-waveform (e.g. obtained by photoplethysmography (PPG)) and blood pressure with assumptions on the elastic properties of the blood vessel walls, is described in WO2017/172978, sections 00108 et seq. to which reference is made for further information.

Various techniques can be used for correlating the pulse-waveform to blood pressure values. For more general and specific information related to correlating pulse waveforms to blood pressure values, reference is made to Xing, Xiaoman, and Mingshan Sun. "Optical Blood Pressure Estimation with Photoplethysmography and FFT-Based Neural Networks", Biomedical Optics Express 7.8 (2016): 3007-3020, and http://cs229.stanford.edu/proj2014/Sharath%20Ananth,Blood%20Pressure%20Detection%20from%20PPG.pdf, each of which are fully incorporated herein.

The pressure sensing monitor or the pressure sensing device in accordance with the present invention may be a wearable device or form a component thereof.

Wearable devices are apparatuses that can be worn directly on the skin in different parts of the body. These devices have gained considerable attention owing to their ease of collecting crucial information in real time regarding a wearer's health, both continuously and non-invasively.

The use of wearable healthcare devices also encourages people to take greater interest in their own healthcare in a more convenient and cheaper way, thereby improving their compliance.

Wearable devices in accordance with the present invention may have a variety of different forms such as e.g. smart wristbands, watches, shirts, shoes, headbands, eyeglasses and necklaces, amongst others. Most of them contain sensors that gather raw data that is fed into a database or software application for analysis.

The wearable device may comprise one or more sensors for determining a variety of different data. Thus, besides the pressure sensing, wearable devices may be used to collect data on calories burned, steps walked, time spent for exercise and two or more of these functions are often combined in a wearable device. Thus, the pressure sensing monitor in accordance with the present invention may constitute the entire wearable device or it may form a part thereof. Furthermore, the pressure sensing device in accordance with the present invention may be combined with other sensing devices in a wearable device.

A review of wearable devices is given in Bao et al., Advanced materials for health monitoring with skin-based wearable devices, Adv. Healthcare Mater. 2017, 6, 1700024- (doi 10.1002/adhm.201700024) to which reference is made for further information.

Another embodiment of the present invention relates to a composite material comprising
a) a porous matrix material comprising a siloxane polymer, comprising a closed porosity volume fraction, and, optionally, an open porosity volume fraction, and
b) a conductive or semiconductive filler substantially present in said closed porosity volume fraction of said porous matrix material a).

What has been said above for the composition, structure and properties for the porous matrix material forming part of the pressure sensing layer and for the filler in accordance with the present invention also applies to the composite material in accordance with the present invention. Accordingly, reference is made here to the description given above for further details.

Another embodiment of the present invention relates to a process for the manufacture of a composite material in accordance with the present invention, comprising the following steps.
a) providing a first non-aqueous phase comprising a siloxane polymer precursor and a curing agent and, optionally, a surfactant,
b) providing a second aqueous phase comprising a conductive filler dispersed in water and, optionally, additives to facilitate and support dispersion of the conductive filler in water,
c) preparing an emulsion by adding aqueous phase b) to the non-aqueous phase a) under stirring,
d) reticulating the product obtained in step c) and, finally,
e) subjecting the product obtained in step d) to a heat treatment to remove the water.

The composite material in accordance with the process of the present invention is obtained by using an inverse emulsion technology wherein the non-aqueous phase is a mixture of monomer and crosslinker and, optionally, a surfactant, and wherein the aqueous phase is an aqueous solution containing the conductive or semiconductive filler and, optionally, a surfactant.

In step a) of the process of the present invention, a non-aqueous phase is prepared by using a siloxane polymer precursor, a curing agent and, optionally, a surfactant.

The siloxane polymer precursor may be preferably a two component kit as described hereinafter.

Two component kits comprising a siloxane precursor polymer and a curing agent are commercially available from a variety of suppliers and the skilled person will select the appropriate precursor products based on his professional knowledge and the needs of the specific application case.

Just by way of example, the principal constitution of such two component kit is explained in more detail for Sylgard® 184.

Sylgard 184® is a silicon elastomer comprising a dimethyl siloxane and an organically modified silica. Sylgard® 184 is prepared by combining a base (Part A) with a curing agent (Part B). The base includes a siloxane (dimethyl-vinyl terminated dimethyl siloxane) and a dimethylvinylated and trimethylated silica) in a solvent (ethyl benzene). The curing agent also includes a mixture of siloxanes and silica in a solvent including dimethyl methyl hydrogen siloxane, dimethyl-vinyl terminated dimethyl siloxane, dimethylvinlylated and trimethylated silica, tetramethyl tetravinyl cyclitetra siloxane and ethyl benzene.

Sylgard® 527 is a silicone elastomer gel substantially similar to Sylgard® 184 but without the silica filler. It is also prepared from a base and a curing agent. A large variety of siloxane compositions are commercially available from various suppliers. The Sylgard® series of products is just one example for such suitable two component kits which may be used in the process of the present invention in step a) and which are commercially available e.g. from Dow Chemical. Another group of suitable curable siloxane polymer precursors are the Elastosil® series of products available from Wacker Chemie.

Exemplary PDMS precursors are vinyl-functional PDMS crosslinkable with hydride-functional crosslinking agents or hydroxyl-functional PDMS crosslinkable with hydride functional crosslinking agents or hydroxyl-functional PDMS crosslinkable in the presence of metal catalysts.

Sylgard® 184 is a particularly preferred siloxane polymer precursor which may be used in the process according to the present invention.

The siloxane precursor may contain one or more excipients selected from the group of catalysts, inhibitors, flow agents, silicone oils, solvents and fillers. In one embodiment the excipient is selected from the group of catalysts (e.g. Pt complexes for addition curing or Sn complexes for condensation curing) or peroxides (peroxide curing).

The non-aqueous phase a) may also optionally comprise a surfactant to stabilize the system. Suitable surfactants for this purpose are known to the skilled person and are available in great variety from a multiplicity of commercial suppliers. The skilled person will, based on his professional expertise select a suitable surfactant.

Just by way of example, silicone alkyl polyethers such as the Silube® series of products may be mentioned here as suitable surfactants. Silicone alykl polyethers are alkylated silicones co-reacted with polyethers. Such surfactants are effective for emulsifying organic oils and silicones with water respectively aqueous phases.

The Silube® products available from Siltech company are represented by the following structure:

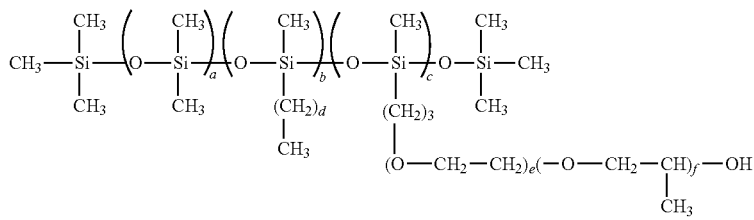

where d = 1-29

The surfactant may be added to the siloxane precursor composition and is usually present in an amount from 0.5 to 10 wt %, preferably of from 0.75 to 7.5 wt % of the total weight of non-aqueous phase a).

In step b) of the process of the present invention, an aqueous phase comprising the conductive or semiconductive filler dispersed therein, is provided.

To obtain the aqueous phase provided in step b), the conductive or semiconductive filler is preferably added to water, preferably deionized water, under stirring or under the application of ultrasound to disperse the conductive filler. When using ultrasound to support homogeneous dispersion of the filler the system is preferably cooled e.g. with an ice bath to avoid excessive heating-up of the system.

The solution prior to addition of the conductive or semiconductive filler may comprise additives to facilitate and support the dispersion of the conductive or semiconductive filler. A preferred surfactant for this purpose, is gum arabic, also known as acacia gum. Acacia gum is a natural gum consisting of the hardened sap of various species of the acacia tree. Gum arabic is a complex mixture of glycoproteins and polysaccharides.

The skilled person is aware of further additives which facilitate and support the dispersion of conductive and semiconductive fillers in aqueous systems and respective products are commercially available in great variety from a number of different suppliers so that no further details have to be given here. The skilled person will select a suitable dispersion aid based on his professional knowledge and experience.

To obtain the emulsion, the aqueous phase provided in step b) is slowly added to the non-aqueous phase provided in step a) under mechanical stirring in step c) of the process.

Fluid undergoes shear when one area of fluid travels with a different velocity relative to an adjacent area. A high-shear mixer uses a rotating impeller or high-speed rotor, or a series of such impellers or inline rotors, usually powered by an electric motor, to work the fluid, creating flow and shear. The tip velocity, or speed of the fluid at the outside diameter of the rotor, will be higher than the velocity at the center of the rotor, and it is this velocity difference that creates shear.

In a preferred embodiment, a high-shear mixer disperses, or transports, the aqueous phase provided in step b) into the main continuous phase provided in step a) with which it would normally be immiscible, thereby creating an emulsion.

The skilled person will select the diameter of the stirrer and its rotational speed (and thereby defining the shear rate applied) in accordance with the needs of the specific application situation and the desired final morphology of the product.

Through the application of high shear rates it has been surprisingly found that it is possible to uniformly distribute high amounts of the non-aqueous phase in the silicone rubber and to form a stable emulsion, said emulsion being stable over extended periods of time.

The weight ratio of the non-aqueous phase to the aqueous phase is not subject to particular limitations and is usually within the range of 1:10 to 10:1, preferably in the range of 1:5 to 5:1. Preferably, the non-aqueous phase forms the continuous phase of the system, in which the aqueous phase is dispersed and the amounts of non-aqueous and aqueous phase are chosen respectively. In such case, the weight of the aqueous phase preferably does not exceed the amount of the non-aqueous phase and is usually in the range of from 30 to 40 wt % of the entire emulsion. In some application cases approximately equal weights of non-aqueous and aqueous phase have been found to provide certain advantages.

After step c) an emulsion is obtained which has droplets of the water phase containing the conductive filler dispersed in the non-aqueous phase. The average diameter of these droplets is usually in the range from 0.1 to 300 μm, preferably in the range of from 0.5 to 150 μm and particularly preferred in the range of from 1 to 30 μm. The mean droplet size obtained depends on the viscosity of the continuous phase.

Solid materials are then obtained in step d) by reticulating (curing) the emulsion obtained in step c) usually at a temperature below the boiling point of water, preferably in the range from 60 to 95° C. for a period of time of 0.5 to 12, preferably from 1 to 8 hours. In some cases, curing times of appr. 4 h have been found to be best. The relative humidity in this step is usually close to 100% or is equivalent to 100%.

In one embodiment, curing may take place in the form of addition-based curing, such as by the use of Pt as a catalyst wherein Si—H groups of the crosslinking agent react with vinyl groups of the silicone polymer.

In accordance with another embodiment, curing may take place in a condensation based system, such as through the use of a Sn based curing system and a room-temperature vulcanizing silicone rubber wherein an alkoxy-crosslinker experiences a hydrolysis step and is left with a hydroxyl group participating in a condensation reaction with another hydroxyl group attached to the polymer in question.

In still another embodiment, curing may take place in a peroxide-based system wherein an organic peroxide compound decomposes at elevated temperatures to form reactive radicals that chemically crosslink the polymer chains.

In the final step, the product obtained in step d) is subjected to a heat treatment to remove the water. As the siloxane polymer formed after curing is permeable to water vapor, the droplets leave a porous structure with the conductive or semiconductive filler being substantially present in the closed porosity volume fraction of the matrix material, preferably with pore walls being coated with the conductive or semiconductive filler, thereby yielding the composite material in accordance with the present invention.

The conditions of curing in step d) and drying in step e) influence the morphology of the porous composite material and the skilled person will select the conditions thereof in a suitable manner to obtain the desired morphology.

Another embodiment of the present invention relates to a film comprising, preferably consisting essentially of, and even more preferably consisting of the composite material in accordance with the present invention.

In accordance with a preferred embodiment, the thickness of the film is in the range from 0.1 to 500 μm preferably in the range of from 5 to 250 μm. The average thickness of the layer is preferably at least 5 μm, more preferably at least 10 μm, more preferably at least 15 μm. In a most preferred embodiment, the average thickness of the layer ranges from 15 μm to 100 μm.

The films in accordance with the present invention (which are the films comprised in the pressure sensing layers in accordance with the present invention) can be obtained by forming the emulsion of step c) of the process in accordance with the present invention into a film by pouring same into a mold before applying step d). The film thus obtained is then subjected to steps d) and e) in accordance with the process of the present invention to obtain the final film suitable for use in pressure sensing devices.

In the final step of the process in accordance with the present invention, the product obtained in step d) is subjected to a heat treatment to remove the water. This heat treatment step is usually carried out at a temperature exceeding the boiling point of water at atmospheric pressure, preferably at a temperature in the range of from 100 to 200° C. and for a duration of from 0.1 h to 5 h, preferably of from 0.5 to 5 hours. In some cases temperatures of 130 to 170° C. and treatment times of 0.75 to 3 h, particularly of from 1 to 2 h have been found to be suitable.

After the final step, a microporous composite material, eventually in film form is obtained, which comprises pores in a closed porosity volume fraction with an average diameter preferably in the range from 0.1 to 200 μm and preferably with the pore walls being lined and the pores being filled with the conductive filler to a certain degree.

A further embodiment of the present invention relates to a substrate coated with a film according to the present invention. This substrate is the substrate comprised in the pressure sensing layer in accordance with the present invention.

The substrate is not subject to particular limitations as structure and composition are concerned and the skilled person will select the substrate taking into account the needs of the specific application situation.

The structure of the substrate may be adopted to the specific intended use and the substrate may have the function of a carrier for the deformable film or it may provide increased mechanical stability for the said film.

The material of the substrate may be metallic or non-metallic respectively insulating or conductive depending on the intended final use of the coated substrate in a pressure sensing device. In some cases, aluminum substrates or substrates comprising aluminum have been found to provide certain advantages.

The coating of the film onto the substrate may be effected using conventional coating techniques known to the skilled person which have been described in the literature so that no further details need to be given here.

Another embodiment of the present invention relates to multilayer systems comprising a first layer of a film in accordance with the present invention, and, adjacent thereto, a second layer which is an insulating layer.

The films comprising the composite material in accordance with the present invention or the substrates coated with such films may exhibit dielectric losses once an amount of conductive filler near to or above the percolation limit is used, which is a certain disadvantage.

The multilayer systems in accordance with the present invention overcome these disadvantages by adding a second layer onto the films in accordance with the present invention which second layer is an insulating layer. Thereby, the high permittivity of the material is maintained while at the same time the conductivity is significantly reduced.

The material of the second insulating layer may be any insulating material which may be formed into a film or a suitable coating on the first layer. For economical and processability reasons, insulating layers of thermoplastic polymers or silicone rubbers are preferred. Polyesters may be mentioned as examples for thermoplastic polymers. Mylar® films based on polyethylene terephthalate polymers, which are commercially available from a number of suppliers, have been found advantageous in terms of processability and costs and thus represent a particularly preferred group of insulating materials for the second insulation layer.

The thickness of the second insulating layer is not subject to particular limitations and often is in the range from 0.1 to 500 μm, preferably in the range from 0.1 to 50 μm, preferably at most 5 μm.

The insulating layer may be spread onto the films comprising the composite material or onto the substrates coated with such films in accordance with the present invention. The insulating layer may itself also be deposited on a substrate.

Coating of the insulating layer onto the film comprising the composite material may be achieved by conventional coating techniques such as spin coating, rotation coating or other coating techniques known to the skilled person and described in the literature.

The pressure sensing layers in accordance with the present invention, the films comprising same and the coated substrates or multilayer structures comprising such films are particularly suitable for use in piezocapacitive devices. Due to their high permittivity and low conductivity, the sensitivity of the devices using said materials is high and very low variations in external pressure can be reliably determined.

When a compressive stress is applied onto the microporous composite material in accordance with the present invention, a large deformation is created as well as a modification of its microstructure. Both effects lead to large variation of the equivalent capacitance and therefore to a large sensitivity at low external pressures e.g. in the range of from 0.1 kPa to 10 kPa. Accordingly, the composites in accordance with the present invention are excellent candidates for capacitive pressure sensing applications, and more specifically for low pressure sensors commonly needed for bio-signals such as blood pressure and heart rate monitoring.

EXAMPLE 1

A solution comprising 5.0 wt % of arabic gum in water was prepared in a flat bottom flask by mixing 5 g of arabic gum (obtained from Sigma Aldrich) with 95 g of deionized water. Magnetic stirring was applied to homogeneously dissolve the arabic gum which served as a surfactant to disperse carbon black powder (the conductive filler). The carbon black used was purchased from Alfa Aesar under the reference 39724-carbon black and was used as received.

The dispersion of the carbon black powder was carried out in a flat-bottom flask by mixing the carbon black powder in the desired amounts and arabic gum solution. The mixture was sonicated for one hour to homogenously disperse the carbon black particles while the solution was cooled in an ice bath to avoid an excessive temperature increase as a result of the sonication. The obtained product was used as the aqueous phase.

As non-aqueous phase, Sylgard® 184 was purchased from Dow Corning as a kit consisting of a PDMS base and a curing agent. The relative dielectric permittivity of the PDMS materials was approximately 2. To the mixture of PDMS base and crosslinker, Silube®J-208-212 was added as a surfactant to reach a concentration of 5 wt % of surfactant.

The aqueous phase was slowly added to the non-aqueous phase under mechanical stirring with a spatula in order to reach a ratio of aqueous phase to non aqueous phase of 50:50.

The water-in-oil emulsion thus obtained was poured into a mold having a depth of 500 μm and a diameter of 24 mm and covered. Thereafter the film was reticulated by subjecting the mold to a temperature of 90° C. for 4 hours in a water bath (to have 100% humidity).

In the final step, the reticulated film was removed from the mold and placed in an oven at a temperature of 150° C. for one hour to remove the water.

The composite material obtained had a microporous structure with pores having an average diameter of from 10 to 30 μm. The average pore size was determined on scanning electron microscopy (SEM) images of the products.

The carbon black content of the composite material ranged from 4.6 to 10.2 wt %, based on the entire weight of the composite material.

The permittivity was determined by broadband dielectric spectroscopy using a sandwich geometry with circular brass electrodes. Measurements were performed at room temperature over frequencies f from 10 Hz to $10^7$ Hz. The real part of the permittivity was 3 for a material without any carbon black, 13.5 for a composite material comprising 4.6 wt % of carbon black. At an amount of 10.2 wt % of carbon black the permittivity was determined to be 4000 but the material was conductive as the concentration exceeded percolation threshold. If the film obtained was formed into a multilayer structure with an insulating film (Mylar film), the permittivity was 330 but the material remained non-conductive.

Static sensitivity was measured in compression using circular stainless steel clamps of diameter 25 mm and acting as electrodes. RSA GII Solids Analyzer was used to maintain a normal pressure on the sample while measuring the complex impedance at 1V and 100 Hz using a Keysight Precision LCR Meter. In order to estimate the equivalent capacitance Cp and resistance Rp of the sample it was assumed that the material acts as the combination of a resistor and a capacitor in parallel. The reference capacitance $C_0$ was arbitrarily defined when 0.1 kPa is applied on the sample. Measurement was performed over pressures ranging from 0.1 kPa up to 70 kPa.

For carbon black concentrations of 4.2 wt % without an insulating layer, $\Delta C/C_o$ reached values in the range from 0.9 to 1.8 in the pressure range from 2 kPa to 10 kPa. If the carbon black concentration was 10% and no insulating layer was present, the value for $\Delta C/C_o$ dropped to values close to 0 at a pressure of 2 kPa. With an insulating layer and a carbon black concentration of 10 wt %, $\Delta C/C_o$ was approximately 1.8 at a pressure of 2 kPa and exceeded a value of four at a pressure of 10 kPa.

The pressure sensor (at a carbon black concentration of 10 wt %) was sensitive to pressure changes from 0.1 kPa up to 1 kPa and this pressure change was associated with a capacitance change of plus 150 pF.

Generally the sensing layers of the present invention are sensitive to very small pressure changes and pressure changes of as low as 0.1 kPa are associated with capacitance changes of 100 pF or more.

These results show the excellent sensitivity of the pressure sensing layers in accordance with the present invention for use in low pressure sensing devices.

LIST OF REFERENCE NUMERALS IN FIGS. 1 TO 7

1 Ground for first and second sensor
2 First sensor
3 Second sensor
4 Third sensor
5 Fourth sensor
6 Ground for third and fourth sensor
20 Multilayer system
21, 31 Protective layer
22, 32 Bottom electrode
23, 33 Pressure sensing first layer or film
231 porous matrix material
232 conductive or semiconductive filler
24, 34 Top electrode
25, 35 Encapsulant
26 second layer
401, 501, 601, 701 Pressure sensing device
402, 502, 602, 702 Electrode(s)
403, 503, 603, 703 Pressure sensing layer
404, 504, 604, 704 Protective layer
405, 505, 605, 705 Changes in capacitance due to pressure changes
406, 506, 606, 706 Signal converting unit
407, 507, 607, 707 Data transmission unit
408, 508, 608, 708 Microcontroller unit
409, 509, 609, 709 Power supply
410, 510, 610, 710 Electronic device
411, 511, 611 Smartphone
412, 512, 612, 712 Communication signals
413, 513, 614, 713 Data transmission unit
414, 514, 614, 714 Means for patient authentification
415, 515, 615, 715 Means for patient notification
416, 516, 616, 716 Means for data analysis
417, 517, 617 Means for result analysis
418, 518, 618, 718 Means for data storage
519, 619, 719 Cloud
520, 620, 720 Internet connection
621, 721 Memory
722 Display device
723 Gateway
724 User Interface

The invention claimed is:

1. A pressure sensing layer comprising a film comprising:
a) a first layer of porous matrix material comprising a siloxane polymer, comprising a closed porosity volume fraction, and an open porosity volume fraction, and
b) a conductive or semiconductive filler present in said closed porosity volume fraction of said first layer of porous matrix material a);

wherein at least 70% and up to 90% of the conductive or semiconductive filler is present in the closed porosity volume fraction.

2. The pressure sensing layer of claim 1, wherein the conductive or semiconductive filler is selected from the group consisting of carbon nanotubes, carbon nanohorns, graphite, graphene and carbon black; or selected from the group consisting of metal particles and intrinsically conducting polymers (ICPs); or selected from the group consisting of Si, Si—Ge, GaAs, InP, GaN, SiC, ZnS, ZnSe, CdSe, CdS, and metal oxide particles.

3. The pressure sensing layer of claim 1, wherein the pressure sensing layer has a thickness in the range of from 0.1 to 500 μm.

4. The pressure sensing layer in accordance with claim 1, wherein the pressure sensing layer comprises a first layer and, adjacent thereto, a second layer which is an insulating layer.

5. The pressure sensing layer in accordance with claim 4 wherein the second layer is a polyester layer.

6. The pressure sensing layer in accordance with claim 1, wherein the pressure sensing layer is a sensing layer for sensing low pressures.

7. A pressure sensing piezocapacitive device comprising at least one electrode and at least one pressure sensing layer in accordance with claim 1.

8. The pressure sensing piezocapacitive device in accordance with claim 7, wherein the pressure sensing piezocapacitive device provides a signal in response to a pressure variation wherein the pressure variation is a pulse wave event.

9. A pressure sensing monitor comprising:
a) at least one pressure sensing layer in accordance with claim 1 providing a capacitance change signal in response to a pressure variation,
b) a power supply,
c) at least one signal converting unit capable of converting the capacitance change signal provided by the pressure sensing layer into an analog or digital electric signal, optionally with filters and amplifiers for the signal,
d) at least one microcontroller unit capable of digitalizing an analog signal provided by signal converting unit c) and/or communicating digitally with the at least one signal converting unit c) and capable to convert the signal obtained from the at least one signal converting unit c) into other formats using suitable algorithms stored in the at least one controlling unit as readable code.

10. The pressure sensing monitor in accordance with claim 9, wherein the pressure variation is a pulse wave event.

11. The pressure sensing monitor in accordance with claim 9 wherein the at least one controlling unit c) converts the signal obtained from the at least one signal converting unit b) into hemodynamic parameters.

12. The pressure sensing monitor in accordance with claim 9, wherein the pressure sensing monitor is a wearable piezocapacitive device.

13. The pressure sensing monitor according to claim 9, wherein the conductive or semiconductive filler of the at least one pressure sensing layer is selected from the group consisting of carbon nanotubes, carbon nanohorns, graphite, graphene and carbon black; or selected from the group consisting of metal particles and intrinsically conducting polymers (ICPs); or selected from the group consisting of Si, Si—Ge, GaAs, InP, GaN, SiC, ZnS, ZnSe, CdSe, CdS, and metal oxide particles.

14. The pressure sensing layer of claim 1, wherein up to 99% of the total content of the conductive or semiconductive filler is present in the closed porosity volume fraction.

15. A composite material comprising:
a) a porous matrix material comprising a siloxane polymer, comprising a closed porosity volume fraction, and an open porosity volume fraction, and
b) a conductive or semiconductive filler substantially present in said closed porosity volume fraction of said porous matrix material a),
wherein at least 70% and up to 90% of the conductive or semiconductive filler is present in the closed porosity volume fraction.

16. The composite material of claim 15, wherein the conductive or semiconductive filler is selected from the group consisting of carbon nanotubes, carbon nanohorns, graphite, graphene, carbon black, metal particles, and intrinsically conducting polymers (ICPs), or selected from the group consisting of Si, Si—Ge, GaAs, InP, GaN, SiC, ZnS, ZnSe, CdSe, CdS, and metal oxide particles.

17. A film comprising the composite material of claim 15, wherein the film has a thickness in the range of from 0.1 to 500 μm.

18. A multilayer system comprising a first layer of a film in accordance with claim 17 and, adjacent thereto, a second layer which is an insulating layer.

19. A pressure sensing piezocapacitive device comprising the composite material in accordance with claim 15.

20. The pressure sensing piezocapacitive device in accordance with claim 19, wherein the pressure sensing piezocapacitive device is a blood pressure sensing device.

21. The pressure sensing piezocapacitive device according to claim 19, wherein the conductive or semiconductive filler of the composite material is selected from the group consisting of carbon nanotubes, carbon nanohorns, graphite, graphene and carbon black; or selected from the group consisting of metal particles and intrinsically conducting polymers (ICPs); or selected from the group consisting of Si, Si—Ge, GaAs, InP, GaN, SiC, ZnS, ZnSe, CdSe, CdS, and metal oxide particles.

22. The pressure sensing piezocapacitive device according to claim 19, comprising a film comprising:
a) a first layer of porous matrix material comprising a siloxane polymer, comprising a closed porosity volume fraction, and an open porosity volume fraction, and
b) a conductive or semiconductive filler present in said closed porosity volume fraction of said first layer of porous matrix material a) and
c) one or more additional layers;
wherein at least 70% and up to 90% of the conductive or semiconductive filler is present in the closed porosity volume fraction.

23. The pressure sensing piezocapacitive device according to claim 19, wherein the conductive filler is selected from the group consisting of carbon nanotubes, carbon nanohorns, graphite, graphene, carbon black.

24. A process for the manufacture of a composite material in accordance with claim 15, the process comprising the following steps:
a) providing a first non-aqueous phase comprising a siloxane polymer precursor and a curing agent and,
b) providing a second aqueous phase comprising a conductive or semiconductive filler dispersed in water,
c) preparing an emulsion by adding aqueous phase b) to the non-aqueous phase a) under stirring,
d) reticulating the product obtained in step c) and, finally, e) subjecting the product obtained in step d) to a heat treatment to remove the water.

25. The composite material of claim 15, wherein up to 99% of the total content of the conductive or semiconductive filler is present in the closed porosity volume fraction.

\* \* \* \* \*